(12) United States Patent
Boinagrov et al.

(10) Patent No.: US 11,944,378 B2
(45) Date of Patent: *Apr. 2, 2024

(54) DEVICES FOR IMAGE-GUIDED LIGHT TREATMENT OF SKIN

(71) Applicant: SCITON, INC., Palo Alto, CA (US)

(72) Inventors: David Boinagrov, Mountain View, CA (US); Frank Garcia, Redwood City, CA (US); Hartmuth Hecht, Moss Beach, CA (US); James L. Hobart, Palo Alto, CA (US); Daniel K. Negus, Palo Alto, CA (US)

(73) Assignee: SCITON, INC., Palo Alto, CA (US)

( * ) Notice: Subject to any disclaimer, the term of this patent is extended or adjusted under 35 U.S.C. 154(b) by 37 days.

This patent is subject to a terminal disclaimer.

(21) Appl. No.: 17/566,794

(22) Filed: Dec. 31, 2021

(65) Prior Publication Data

US 2022/0117661 A1    Apr. 21, 2022

Related U.S. Application Data

(63) Continuation of application No. 16/076,982, filed as application No. PCT/US2017/017571 on Feb. 11, 2017, now Pat. No. 11,219,485.
(Continued)

(51) Int. Cl.
*A61B 18/20*    (2006.01)
*A61N 5/06*    (2006.01)
(Continued)

(52) U.S. Cl.
CPC .......... *A61B 18/203* (2013.01); *A61N 5/0616* (2013.01); *A61N 5/0617* (2013.01);
(Continued)

(58) Field of Classification Search
CPC .................. A61B 18/20; A61B 18/203; A61B 2018/00452; A61B 2018/00476;
(Continued)

(56) References Cited

U.S. PATENT DOCUMENTS 7,309,335 B2    12/2007  Altshuler et al.
11,213,350 B2*    1/2022  Boinagrov ........... A61N 5/0616
(Continued)

OTHER PUBLICATIONS

International Search Report and Written Opinion issued in counterpart PCT Application No. PCT/US2017/017571 dated May 2, 2017 (eleven (11) pages).

*Primary Examiner* — Jon Eric C Morales
(74) *Attorney, Agent, or Firm* — Maynard Nexsen PC; John P. Zimmer; Nicholas P. Stadnyk

(57) ABSTRACT

In one aspect, devices for light treatment of skin are described herein. A device described herein, in some embodiments, comprises an interior compartment having a proximal end and a distal end, and an optical aperture disposed at the distal end. The device also comprises a laser or BBL source that produces a laser or BBL beam. The laser or BBL beam has a first optical path within the interior compartment, between the proximal end and the distal end. Additionally, the first optical path exits the interior compartment through the optical aperture. The device further comprises a camera that receives light from the aperture. The light received from the aperture has a second optical path within the interior compartment. Further, a selectively reflective optical element is disposed in the first and second optical paths. The selectively reflective optical element generally transmits the laser or BBL beam but generally reflects at least a portion of the light from the aperture toward the camera.

12 Claims, 2 Drawing Sheets

Related U.S. Application Data

(60) Provisional application No. 62/294,915, filed on Feb. 12, 2016.

(51) Int. Cl.
  *A61B 18/00* (2006.01)
  *A61B 18/18* (2006.01)
  *A61N 5/067* (2006.01)

(52) U.S. Cl.
  CPC .............. *A61B 2018/00458* (2013.01); *A61B 2018/00476* (2013.01); *A61B 2018/00577* (2013.01); *A61B 2018/00589* (2013.01); *A61B 2018/00904* (2013.01); *A61B 2018/1807* (2013.01); *A61B 2018/202* (2013.01); *A61N 2005/0626* (2013.01); *A61N 2005/0644* (2013.01); *A61N 5/067* (2021.08)

(58) Field of Classification Search
  CPC ........ A61B 2018/00904; A61B 5/0066; A61B 5/0068; A61B 5/1072; A61B 5/417; A61B 5/441; A61B 5/448
  See application file for complete search history.

(56) References Cited

U.S. PATENT DOCUMENTS

| | | | |
|---|---|---|---|
| 11,219,485 B2* | 1/2022 | Boinagrov | A61B 18/203 |
| 2004/0030325 A1 | 2/2004 | Cahir | |
| 2007/0179481 A1 | 8/2007 | Frangineas | |
| 2010/0063491 A1 | 3/2010 | Verhagen et al. | |
| 2011/0196365 A1 | 8/2011 | Kim | |
| 2012/0330222 A1 | 12/2012 | Makin et al. | |
| 2013/0023966 A1 | 1/2013 | Depfenhart et al. | |
| 2014/0023993 A1 | 1/2014 | Zeng et al. | |
| 2014/0039473 A1 | 2/2014 | Liu et al. | |
| 2015/0045723 A1 | 2/2015 | Paithankar | |
| 2015/0298254 A1 | 10/2015 | Varghese et al. | |
| 2022/0125513 A1* | 4/2022 | Boinagrov | A61N 5/0616 |

* cited by examiner

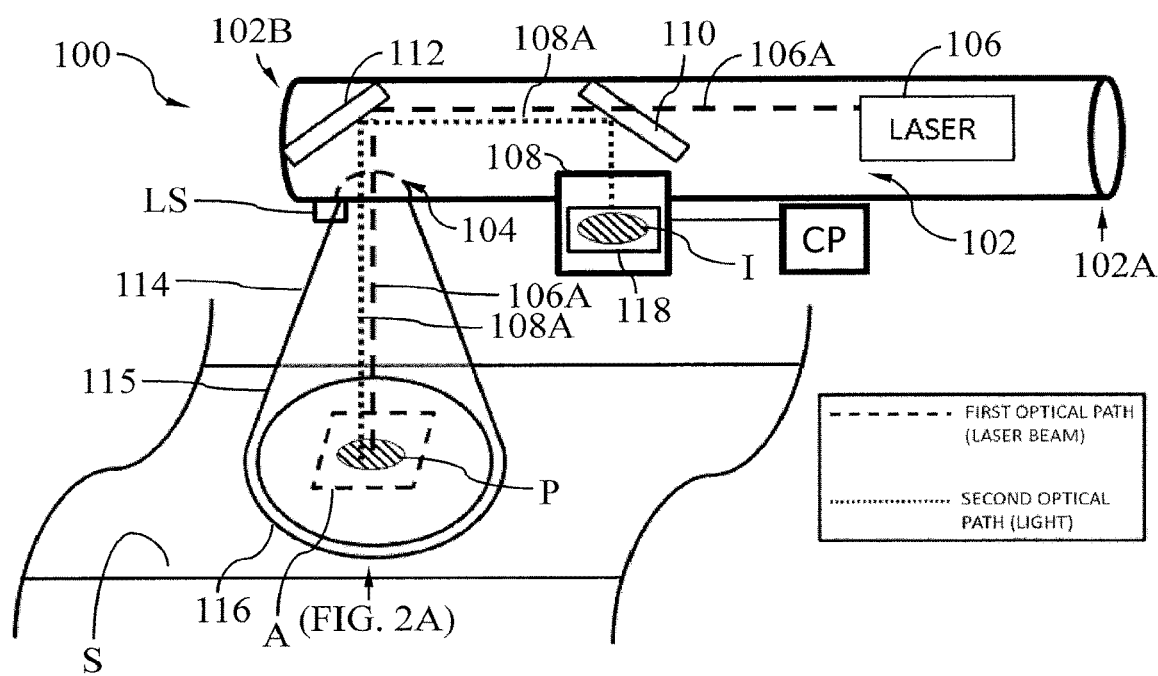
FIG. 1
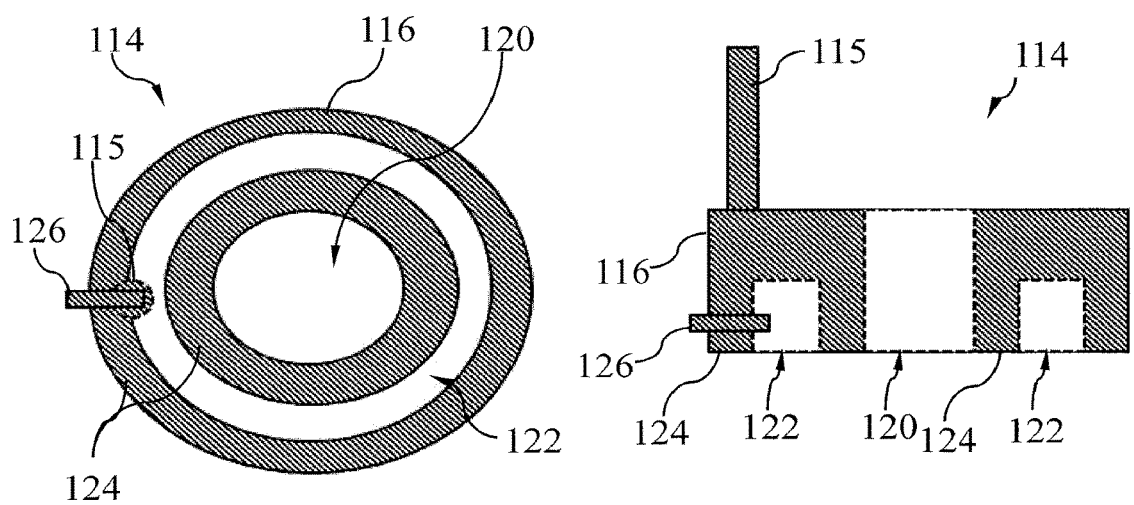
FIG. 2A　　　　　FIG. 2B

DEVICES FOR IMAGE-GUIDED LIGHT TREATMENT OF SKIN

CROSS REFERENCE TO RELATED APPLICATIONS

This application is a continuation application of U.S. application Ser. No. 16/076,982 filed Aug. 9, 2018, which is a 35 U.S.C. § 371 U.S. national phase entry of International Application No. PCT/US2017/017571 having an international filing date of Feb. 11, 2017, which claims priority pursuant to 35 U.S.C. § 119 to U.S. Provisional Patent Application Ser. No. 62/294,915, filed on Feb. 12, 2016, which are hereby incorportaed by reference in llitslitheir entiretyentireties.

FIELD

This invention relates to devices and methods for treating skin and, in particular, to devices and methods for the treatment of skin with lasers.

BACKGROUND

Many skin conditions can be treated with lasers. In general, laser light is selectively delivered to specific areas of the skin in such treatment methods. Selective and precise delivery of laser light to a specific area of skin can improve safety, increase treatment efficacy, and minimize adverse, undesired effects of treatment. However, in many treatments, target areas of skin are very small. For example, in some cases, target areas of skin have dimensions of less than one millimeter. Thus, laser treatment of skin often requires microscopically precise targeting of laser light. Unfortunately, many current laser treatment devices are not capable of such precise delivery of laser light to skin. There is accordingly a need for improved devices and methods for precisely delivering laser light to desired areas of skin.

In hyperhidrosis, an excess of sweating is observed in certain areas of the skin, including in the axilla, on the palms of the hands, and on the soles of the feet. One common way to address hyperhidrosis is the use of deodorants and/or antiperspirants. However, the action or effectiveness of deodorants and antiperspirants are often limited to several hours. Other existing treatment methods of hyperhidrosis include surgical removal of sweat glands from under the skin, application of a botulinum toxin, or destruction of sweat pores by the application of electromagnetic radiation in the microwave region of the spectrum. While these techniques can be effective in certain cases, these techniques can also suffer from one or more disadvantages. For example, the use of a botulinum toxin is currently not cleared for palms and soles, and treatment with a botulinum toxin provides only temporary relief of symptoms. As another example, the use of microwave radiation is associated with high tissue morbidity. Thus, there is a need for improved devices and methods for treating various skin conditions such as hyperhidrosis or unwanted hair, including in a manner that is safe, efficient, and/or permanent.

SUMMARY

In one aspect, devices and methods for treating skin are described herein which, in some cases, can provide one or more advantages compared to some other devices and methods. For example, in some embodiments, a device described herein can enable the precise delivery of laser light to a desired region of skin or other target surface. Additionally, in some embodiments, a method described herein can treat a variety of skin conditions through the precise targeting and/or destruction of various skin components, such as eccrine glands or hair follicles. Moreover, devices and methods described herein can combine laser delivery with skin imaging in a single device and/or process. Additionally, in some cases, a method or device described herein provides automated visual identification of skin treatment targets followed by computer- and opto-mechanically-guided laser treatment of the identified targets. Methods and devices described herein can also provide safe, efficient, and/or permanent treatment of various skin conditions or diseases.

In one aspect, devices for the laser treatment of skin (or other targets or surfaces) are described herein. In some embodiments, such a device comprises an interior compartment having a proximal end and a distal end, and an optical aperture disposed at the distal end. The device also comprises a laser or Broad Band Light (BBL) source that produces or is positioned or configured to produce a laser or BBL beam. The BBL source can be produced from an intense flashlamp derived incoherent light beam, which is sometimes called Intense Pulsed Light (IPL). For reference purposes herein, the term "BBL" will be used to refer to BBL and IPL, such that the two terms are interchangeable. The laser or BBL beam has a first average wavelength and a first optical path within the interior compartment of the device, between the proximal end and the distal end of the device. Additionally, the first optical path of the laser or BBL beam exits the interior compartment of the device through the optical aperture. A device described herein can also comprise a light source that illuminates an area targeted and/or imaged by the device. Moreover, the device further comprises a camera. The camera receives light, or is positioned or configured to receive light from or through the optical aperture. The light received from or through the optical aperture has a second average wavelength and a second optical path within the interior compartment of the device. The second average wavelength of the light received from or through the optical aperture generally differs from the first average wavelength of the laser or BBL beam. The first optical path of the laser or BBL beam also generally differs, at least in part, from the second optical path of the light received by the camera from or through the optical aperture of the device. In addition, a device described herein further comprises a selectively reflective optical element, such as a selectively reflective plate. The selectively reflective optical element is disposed in both the first optical path and also in the second optical path. Moreover, the selectively reflective optical element transmits at least 70% of the total intensity of the laser or BBL beam incident on the selectively reflective optical element, or is at least 70% transparent to the first average wavelength of the laser or BBL beam. Additionally, the selectively reflective optical element also reflects to the camera at least a portion of the incident light received from the optical aperture. More particularly, the selectively reflective optical element can reflect to the camera a sufficient amount of incident light received from the aperture to permit the camera to receive, record, construct, and/or process an image from the reflected light. The image generally corresponds to at least a portion of a targeted and/or imaged area of skin or a surface of skin. In some cases, the selectively reflective optical element reflects to the camera at least 1% of the total intensity of incident light received from the optical aperture, or is at least 1% reflective to the second average wavelength of the light received from or through the optical aperture.

Moreover, in some cases, a device described herein further comprises an applicator attached to the distal end of the interior chamber. The applicator is configured to couple, connect, or attach the device to a surface of skin of a patient, including for laser or BBL beam delivery to the surface of skin and/or imaging of the surface of skin. In some embodiments, the applicator comprises a bottom surface adjacent to or in direct contact with the surface of skin, and the bottom surface comprises a window that is substantially transparent to the laser or BBL beam and to the light received by the camera. Additionally, the bottom surface of the applicator can be substantially flat or planar. The bottom surface of the applicator may also be conformal to the surface of skin. Further, in some instances, the bottom surface of the applicator comprises an adhesive for reversibly adhering the bottom surface of the applicator to the surface of skin. In addition, in some embodiments, the applicator comprises a non-permeable chamber and the bottom surface of the applicator forms one or more hermetic seals with the surface of skin. The non-permeable chamber of the applicator may also be in fluid communication with a vacuum pump for supplying a vacuum to an interior of the non-permeable chamber, thereby preventing or minimizing lateral movement of the device relative to the surface of the skin being treated and/or imaged. Further, in some cases, the applicator tracks relative movement of the surface of skin of the patient in one or more lateral directions relative to the optical aperture of the device.

A device described herein can also comprise one or more additional components. For example, in some embodiments, a device described herein further comprises computer hardware and/or software for identifying a spatial location of one or more structures, components, or constituents of skin (where the terms "structures," "components," and "constituents" of skin can be used interchangeably) proximate the distal end of the device. The device may also comprise computer hardware and/or software for identifying or determining a class or type, size, shape, color, estimated depth, and/or shaft angle of one or more skin constituents. Further, the hardware and/or software can comprise software for correcting and/or calibrating image non-linearities or distortions from the second optical path or discrepancies in a mechanical model used during image processing. Additionally, the computer hardware and/or software can be mechanically and electrically coupled to the camera of the device, including for processing image data and/or transmitting the image data for further processing, presentation, or display.

A device described herein may also include one or more lenses, mirrors, and/or actuators for directing the light received from the optical aperture to the camera and/or for directing the laser or BBL beam to one or more desired locations on a surface of skin of a patient. Additionally, computer hardware and/or software of a device described herein can also be used to control the foregoing components so as to direct the laser or BBL beam to a desired location within a treatment area of the skin of the patient, as described further below.

In another aspect, methods of treating skin or structures, components, or constituents of skin with a laser or BBL source are described herein. In some cases, such a method comprises removing, destroying, ablating, vaporizing, or coagulating (which can collectively be referred to as "treating") a specific structure, component, or constituent of skin of a patient, including in a specific treatment area targeted by or in contact with a device described herein. Additionally, in some embodiments, a treated structure or constituent of skin is visually labeled or imaged prior to removal or ablation. As described further hereinbelow, such labeling and imaging of a structure or constituent of skin can permit precise treatment of skin. In some cases, a method described herein comprises applying a contrast agent to a treatment area of skin of a patient to produce a labeled structure of the skin. The method further comprises detecting the labeled structure of the skin in an image of the treatment area, and using the image to apply electromagnetic radiation to the labeled structure. However, in other embodiments, a structure of skin can be imaged without the use of a contrast agent. In some such cases, one or more "native" or naturally occurring features of the skin structure are used to visually identify the skin structure. Additionally, in some instances, the electromagnetic radiation used in a method described herein is a laser or BBL beam produced by a device described herein. It is to be understood that the laser or BBL beam or other electromagnetic radiation is applied to the labeled or unlabeled structure of the skin at a power and for a duration sufficient to remove, ablate, vaporize, destroy, coagulate, or otherwise therapeutically treat the labeled or unlabeled structure of the skin, or a portion thereof. In this manner, the labeled or unlabeled structure of the skin can be removed, ablated, vaporized, destroyed, or otherwise treated or rendered non-harmful to the patient, including within the targeted treatment area of the skin. As described further hereinbelow, methods described herein can be used to treat various skin structures or constituents and/or various skin-related disorders or conditions. For example, in some embodiments, a structure described herein is a pore, gland, hair follicle, acne, skin lesion (which may be benign, pre-malignant, or malignant), blood vessel, or vascular lesion. In some such cases, the gland is an eccrine sweat gland, apocrine gland, apoeccrine gland, or sebaceous gland.

These and other embodiments are described in more detail in the detailed description which follows.

BRIEF DESCRIPTION OF THE FIGURES

FIG. 1 is a schematic diagram of a device for laser treatment of skin according to one embodiment described herein.

FIGS. 2A and 2B are, respectively, plan and sectional views of a portion of a device for laser treatment of skin according to one embodiment described herein.

DETAILED DESCRIPTION

Figure 3:
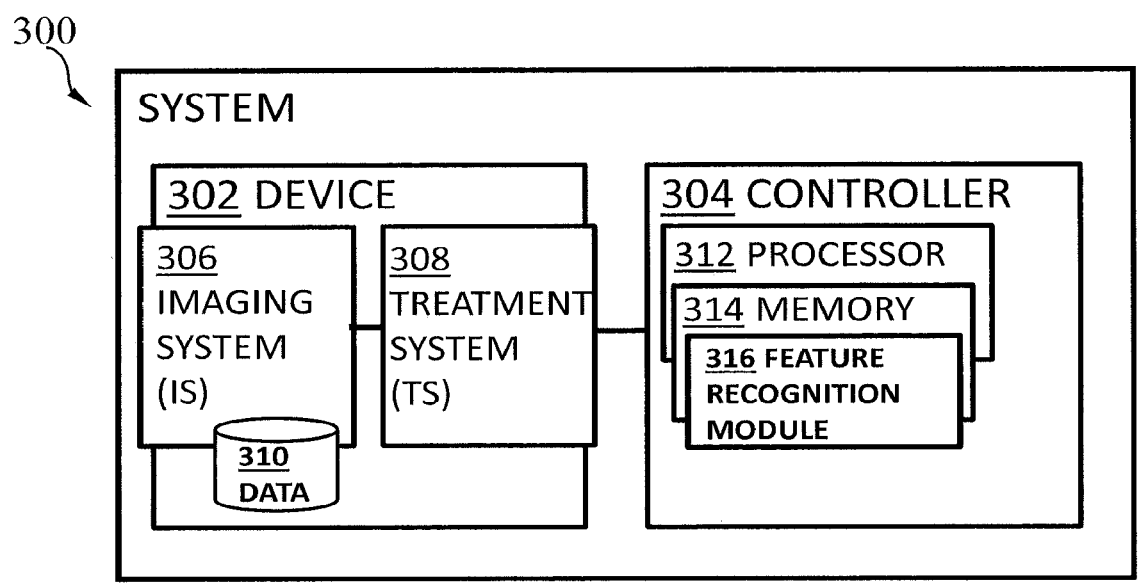
FIG. 3 is a block diagram of an exemplary system for laser treatment of skin according to some embodiments described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Devices for Laser Treatment of Skin

In one aspect, devices for the laser treatment of skin (or other targets or surfaces) are described herein. In some embodiments, such a device comprises an interior compartment having a proximal end and a distal end, and an optical aperture disposed at the distal end. The device also comprises a laser that produces, or is positioned or configured to produce, a laser or BBL beam. The laser or BBL beam has a first optical path within the interior compartment of the device, between the proximal end and the distal end of the interior compartment. Additionally, the first optical path of the laser or BBL beam exits the interior compartment through the aperture. The device further comprises a camera that receives, or is positioned to receive, light from the aperture. The light received from the aperture has a second optical path within the interior compartment. In addition, a device described herein further comprises a selectively reflective optical element disposed in both the first optical path and also in the second optical path. The selectively reflective optical element generally transmits the laser or BBL beam incident on the selectively reflective optical element, and also reflects to the camera at least a portion of the incident light received from the optical aperture. A device described herein can also include an applicator attached to the distal end of the interior chamber. The applicator is configured to couple the device to a surface of skin of a patient, including for laser or BBL beam delivery to the surface of skin and/or imaging of the surface of skin, as described further herein. Moreover, in some cases, a device described herein further comprises one or more additional components, such as computer hardware and/or software for identifying a spatial location of one or more structures or constituents of skin proximate the distal end of the device and/or for directing the laser or BBL beam to one or more desired locations on a surface of skin of a patient. Such hardware and/or software can be used to control or actuate one or more additional components of a device described herein, such as one or more lenses, mirrors, and/or actuators.

Specific components of devices described herein will now be described in further detail. Exemplary devices according to the present disclosure are also described in the specific Examples hereinbelow, including with reference to the drawings.

Turning now to specific components, devices described herein comprise an interior compartment. The interior compartment can have any size and shape not inconsistent with the objectives of the present disclosure. In some cases, the interior compartment defines, comprises, consists of, consists essentially of, or is an interior volume or region of a handpiece. Such a handpiece can be a laser or BBL treatment handpiece including a proximal end or a grip portion or member for gripping by a user of the handpiece. A handpiece can also include a distal end or head portion or member from which a laser is directed toward a target, such as a target treatment area described herein. Additionally, a handpiece described herein, in some embodiments, is attached to one or more additional components of a laser treatment system, such as a power source. Moreover, a handpiece and/or interior compartment of a device described herein can be foil red from any material not inconsistent with the objectives of the present disclosure. For instance, in some cases, the handpiece and/or interior compartment is formed form a metal, plastic, a composite material (such as a fiber glass material), or a combination of two or more of the foregoing.

Devices described herein also comprise an optical aperture disposed at the distal end of the interior compartment of a device described herein. An "optical aperture," for reference purposes herein comprises an opening in the interior compartment that is used for the ingress and/or egress of light (such as laser light and/or light received from a target area for imaging purposes) into and/or from the interior compartment. The optical aperture can have any size or shape not inconsistent with the objectives of the present disclosure. In some instances, the optical aperture has a size sufficiently large to allow a laser or BBL beam described herein to exit the interior compartment of the device and also sufficiently large to permit the receipt of light from a target area for imaging purposes, including in a manner described herein. For example, in some, cases, an optical aperture or opening described herein has a size in one or two dimensions (e.g., a diametrical dimension, or length and width dimensions in a plane of the opening) of up to 5 cm, up to 3 cm, up to 2 cm, up to 1 cm, up to 0.5 cm, or up to 0.1 cm. Other dimensions are also possible. Further, in some embodiments, an optical aperture described herein has a round or circular shape.

Additionally, devices described herein comprise a laser or BBL source positioned or configured to produce a laser or BBL beam. It is to be understood that a "laser" can refer to a single lasing device that produces a single beam of laser light from a single lasing medium. Similarly, as understood by one of ordinary skill in the art, the terms "BBL" source and "BBL beam" can refer to a source and beam, respectively, of intense, broad-spectrum pulses of light, including as IPL is defined and approved by the U.S. Food and Drug Administration. More particularly, a BBL beam produced by a BBL source can comprise pulses of non-coherent or non-laser light having a wavelength from 500 nm to 1200 nm, as described, for instance, in Raulin et al., "IPL technology: a review," *Lasers Surg. Med.* 2003, 32:78-87. Any laser, BBL source, laser beam, or BBL beam not inconsistent with the objectives of the present disclosure can be used. Moreover, the choice of laser, BBL source, or laser or BBL beam can be based on a desired effect of the laser or BBL beam and/or on a desired target of the laser or BBL beam. In some cases, for example, the beam is ablative, such as may be desired for destroying or removing a target component or constituent of skin. Alternatively, in other embodiments, the beam is non-ablative. The beam may also be coagulative, where a "coagulative" beam is understood to cause coagulation of tissue in a target area described herein. Further, in some embodiments, the laser of a device described herein comprises a hybrid laser operable to produce laser beams having a plurality of differing wavelengths. For instance, in some cases, the hybrid laser is operable to selectively produce an ablative laser beam and a coagulative laser beam. It is also possible to use both a BBL source and a laser in the same device. Thus, in some embodiments, a single device described herein can be used to produce and deliver one or more beams (e.g., one or more laser beams, or one or more laser beams in combination with a BBL beam) having a range of properties, as needed for a specific treatment or other application of the device.

A laser of a device described herein may also be a pulsed laser or a continuous wave (CW) laser. Moreover, when a pulsed laser is used, the laser can produce time-modulated pulses of the laser beam. For instance, in some cases, the laser beam comprises an ablative laser beam and the laser produces time-modulated pulses of the ablative laser beam. Not intending to be bound by theory, it is believed that the use of such a pulsed laser beam can provide both ablation and coagulation. More particularly, in some embodiments, time-modulated pulses of an ablative laser beam produce tissue ablation in an ablation area, followed by tissue coagulation around the ablation area.

A laser or laser beam of a device described herein can have any power and any peak or average emission wavelength not inconsistent with the objectives of the present disclosure. For example, in some embodiments, a laser or laser beam of a device described herein has a peak or average emission wavelength in the infrared (IR) region of the electromagnetic spectrum. In some such cases, the laser or laser beam has a peak or average emission wavelength in the range of 1-4 µm, 1-3 µm, 2-4 µm, 2-3 µm, 8-12 µm, or 9-11 µm. For example, in some embodiments, the laser or laser beam comprises an erbium-doped yttrium aluminum garnet (Er:YAG) laser or laser beam or a neodymium-doped YAG (Nd:YAG) laser or laser beam having a peak or average emission wavelength of 2940 nm or 1064 nm. In other cases, the laser or laser beam comprises a carbon dioxide laser or laser beam. A laser beam described herein can also have a peak or average emission wavelength in the visible region of the electromagnetic spectrum. Non-limiting examples of peak or average emission wavelengths suitable for use in some embodiments described herein include 532 nm, 695 nm, 755 nm, 1064 nm, and 1470 nm (e.g., for non-ablative application), or 2940 nm (e.g., for ablative application). Further, in some instances, a laser or laser beam of a device described herein has an average power of 1 to 100 W (e.g., when used for coagulation) or 5 to 200 W (e.g., when used for ablation).

Moreover, the spot size of a laser beam produced by a laser described herein may also vary. Any spot size not inconsistent with the objectives of the present disclosure may be used. In some cases, for instance, the spot size is 0.1-10 mm, 0.1-1 mm, 0.1-0.5 mm, 0.5-5 mm, 1-10 mm, or 1-5 mm. Other spot sizes may also be used.

A BBL source of a device described herein generally produces a pulsed light output. In some cases, the BBL source comprises a xenon gas-filled chamber. In such instances, the BBL source can produce a BBL beam by the application of bursts or pulses of electrical current through the xenon-containing chamber.

It is further to be understood that the depth of tissue ablation, removal, or destruction performed by a laser or BBL source described herein can vary. Any depth not inconsistent with the objectives of the present disclosure may be used. For example, in some embodiments, a laser or BBL ablation step removes at least 90%, at least 95%, at least 98%, or at least 99% of tissue of a targeted skin component, constituent, or area to a depth of up to 1000 µm or to a depth of up to 2000 µm. In some cases, an ablation step removes at least 90%, at least 95%, at least 98%, or at least 99% of tissue of a targeted skin component, constituent, or area to a depth of 50-2000 µm, 50-1000 µm, 50-500 µm, 50-300 µm, 50-200 µm, 75-500 µm, 100-2000 µm, 100-1000 µm, 100-500 µm, 100-300 µm, 100-200 µm, 200-2000 µm, 200-1000 µm, 200-500 µm, 400-2000 µm, 400-1000 µm, 500-2000 µm, 500-1000 µm, or 1000-2000 µm. Other depths are also possible, and the depth is not particularly limited. Further, it is to be understood that "removing" tissue includes ablating, vaporizing, destroying, and otherwise removing the tissue.

As described further herein, a laser or BBL beam produced by a laser or BBL source of a device described herein generally has an optical path within the interior compartment of the device between the proximal end and the distal end of the device. Further, the optical path exits the interior compartment through the optical aperture. The optical path can have any length and/or shape not inconsistent with the objectives of the present disclosure, and the precise length and/or shape of the optical path is not particularly limited.

In some embodiments, a device described herein also comprises a light source other than the laser or BBL source described above. In particular, a device described herein can comprise a light source for illuminating an area or surface that is to be imaged and/or treated by the device. Any light source not inconsistent with the objectives of the present disclosure may be used. For instance, in some cases, the light source comprises or is a non-laser light emitting diode or device (LED). The light source may also be an incandescent or fluorescent light bulb. Other light sources may also be used. Additionally, the light source of a device described herein can be positioned or located on any portion of the device not inconsistent with the objectives of the present disclosure, provided that the light source is capable of illuminating the target area of the device. For example, in some embodiments, the light source is positioned or located adjacent to the optical aperture of the device. Other locations of the light source are also possible.

Devices described herein further comprise a camera. In some cases, the camera is positioned or configured to receive light from the optical aperture of the device. The light can have a second average wavelength. Additionally, in some embodiments, the light can have a second optical path within the interior compartment. It is also possible, in some cases, for the camera to be positioned or configured to receive light from a target area without receiving light through the optical aperture. For instance, in some cases, a camera of a device described herein produces or records an image of a target area using an optical path that is outside of the interior compartment of the device in which the first optical path of the laser or BBL beam is located. In some instances, such a camera is placed or positioned outside of the interior compartment of the device. For example, the camera can be attached to an exterior portion of a handpiece or other portion of a device described herein. In some such cases, the camera is directed to receive light from and/or image a target area of a surface of skin (or other surface) that can be treated with a laser or BBL beam of the device in a manner described herein.

Any camera not inconsistent with the objectives of the present disclosure may be used, regardless of whether the camera is positioned to receive light and/or image a target area along an optical path within an interior compartment of a device described herein, or outside of the interior compartment. For example, in some cases, the camera comprises a digital camera capable of capturing, recording, and/or processing two-dimensional or three-dimensional images of a target area. Further, a camera described herein can be a visible light camera or an infrared camera. Other cameras may also be used.

Devices described herein, in some cases, also comprise a selectively reflective optical element disposed in the first optical path and in the second optical path, wherein the selectively reflective optical element generally transmits the laser or BBL beam incident on the optical element. For example, in some cases, the selectively reflective optical element transmits at least 70% of the laser or BBL beam incident on the selectively reflective optical element, or is at least 70% transparent to the first average wavelength of the laser or BBL beam. Moreover, the selectively reflective optical element generally reflects light to the camera from an imaged target area and/or from an optical aperture of the device. For instance, in some embodiments, the selectively reflective optical element reflects to the camera at least 1% of the total intensity of incident light received from an imaged area and/or optical aperture, or is at least 1% reflective to the second average wavelength of the light received through the optical aperture or otherwise received from the imaged area, which may be the targeted area. In some cases, the selectively reflective optical element has optical properties in accordance with Tables I and II below.

TABLE I

Percentage of Laser or BBL Beam Transmitted by Selectively Reflective Optical Element or Percent Transparency of the Selectively Reflective Optical Element to the Average or Peak Wavelength of the Laser or BBL Beam.

| Percentage of Laser or BBL Beam Transmitted (based on total incident intensity) | Percent Transparency of Optical Element to Laser or BBL Beam (based on total incident intensity) |
|---|---|
| ≥30% | ≥30% |
| ≥50% | ≥50% |
| ≥60% | ≥60% |
| ≥70% | ≥70% |
| ≥75% | ≥75% |
| ≥80% | ≥80% |
| ≥85% | ≥85% |
| ≥90% | ≥90% |
| ≥95% | ≥95% |
| ≥99% | ≥99% |

TABLE II

Percentage of Light from the Aperture or Imaged Area Reflected by Selectively Reflective Optical Element or Percent Reflectance of the Selectively Reflective Optical Element to the Average or Peak Wavelength of the Light Received from the Aperture or Imaged Area.

| Percentage of Light Reflected to Camera (based on total incident intensity) | Percent Reflectance of Optical Element to Light (based on total incident intensity) |
|---|---|
| ≥1% | ≥1% |
| ≥5% | ≥5% |
| ≥10% | ≥10% |
| ≥20% | ≥20% |
| ≥30% | ≥30% |
| ≥40% | ≥40% |
| ≥50% | ≥50% |
| ≥60% | ≥60% |
| ≥70% | ≥70% |
| ≥80% | ≥80% |
| ≥90% | ≥90% |
| ≥95% | ≥95% |
| 10-90% | 10-90% |
| 10-80% | 10-80% |
| 20-90% | 20-90% |
| 30-90% | 30-90% |
| 60-90% | 60-90% |

Moreover, any selectively reflective optical element not inconsistent with the objectives of the present disclosure may be used. Further, the optical element can have any size, shape, and/or structure not inconsistent with the objectives of the present disclosure. In some embodiments, for instance, the selectively reflective optical element comprises or is a selectively reflective plate. In some embodiments, the selectively reflective optical element comprises a dichroic optical element or plate.

In addition, in some cases, a device described herein further comprises an applicator. As described further herein, the applicator can be used to connect or help position one or more components of a device described herein relative to a surface that is targeted and/or treated by the device. For instance, in some cases, the applicator of a device helps align an optical aperture of the device with a target area of skin, including in a manner that permits precise imaging and/or laser or BBL treatment of the target area or constituents or substructures present in the target area. In some embodiments, a device described herein comprises an applicator attached to the distal end of the interior chamber, wherein the applicator is configured to couple, connect, or attach device to a surface of skin of a patient. Such an applicator can have any structure or configuration not inconsistent with the objectives of the present disclosure. For instance, in some cases, the applicator comprises a bottom surface adjacent to the surface of skin. The bottom surface can be substantially flat or planar, such as may be the case when the bottom surface is formed from a rigid material such as a rigid plastic or metal material. The bottom surface may also be conformal to the surface of skin, such as may be the case when the bottom surface is formed from a flexible or drapable material. Moreover, in some embodiments, the bottom surface comprises a window that is substantially transparent to the laser or BBL beam and/or to the light received by the camera. A window that is "substantially" transparent to the laser or BBL beam and/or to the light received by the camera can transmit at least 40%, at least 50%, at least 60%, at least 70%, at least 80%, at least 90%, or at least 95% of the laser or BBL beam and/or the light received by the camera, where the percent transmission can be based on total intensity of the laser or BBL beam and/or light received by the camera that is incident on the window. Additionally, in some embodiments, the bottom surface of an applicator described herein can have a cutout or gap that allows passage of a laser or BBL beam, illumination light, and/or camera light described herein.

Further, an applicator described herein can be reversibly attached to a surface of skin of a patient (or to another surface). For instance, in some cases, the bottom surface of the applicator comprises or is coated with an adhesive for reversibly adhering the bottom surface of the applicator to the surface of skin. Any adhesive not inconsistent with the objectives of the present disclosure may be used. Non-limiting examples of adhesives suitable for use in some embodiments described herein include surgical adhesives such as those described in Duarte et al., "Surgical adhesives: Systematic review of the main types and development forecast," *Progress in Polymer Science*, vol. 37, no. 8 (2012), pages 1031-1050. Such adhesives may include natural or biological adhesives, synthetic or semi-synthetic adhesives, and biomimetic adhesives. In some embodiments, an adhesive described herein comprises a cyanoacrylate adhesive such as a DERMABOND adhesive (available from Ethicon). In other instances, an applicator described herein is reversibly attached to a surface of skin of a patient (or to another surface) by a pressure differential or vacuum. For example, in some such cases, the applicator of a device described herein comprises a non-permeable chamber, and the bottom surface of the applicator forms one or more hermetic seals with the surface of skin. Additionally, the non-permeable chamber of the applicator can be in fluid communication with a vacuum pump for supplying a vacuum to an interior of the non-permeable chamber. In some such instances, the vacuum supplied to the interior of the non-permeable chamber is strong enough to hold the applicator in place, but not strong enough to readily cause bruising of the skin during a clinically relevant period of time. For example, in some embodiments, the vacuum supplied to the interior of the non-permeable chamber is 0.10-0.40 atmospheres (atm) or 0.10-0.20 atm.

An applicator of a device described herein, in some cases, prevents relative movement, or tracks relative movement, of the surface of skin of the patient in one or more lateral directions relative to the optical aperture of the device. In this manner, an applicator described herein can help ensure that a laser or BBL beam directed toward a target area on the surface of skin is delivered precisely and accurately, including under clinical conditions in which a patient may be moving.

Devices described herein, in some embodiments, also comprise computer hardware and/or software for carrying out one or more diagnostic, imaging, and/or treatment steps described herein. Thus, in some cases, a device described herein can be at least partially automated. For example, in some cases, a device is configured to carry out an imaging and/or treatment process according to instructions provided by a computer as a function of space and/or time. The computer can include a processor and a memory storing computer-readable program code portions that, in response to execution by the processor, cause instructions to be provided to one or more components of a device in a desired sequence. Any hardware and/or software not inconsistent with the objectives of the present disclosure may be incorporated into or used with a device described herein. Moreover, various suitable hardware and software components will be readily apparent to those of ordinary skill in the art. Such hardware and/or software can also be used to carry out any step or computational task not inconsistent with the objectives of the present disclosure. For instance, in some cases, a device comprises computer hardware and/or software for identifying a spatial location of one or more constituents of skin proximate the distal end of the device, and/or treating the one or more constituents of skin following identification. The device may also comprise computer hardware and/or software for identifying or determining a class or type, size, shape, color, estimated depth, and/or shaft angle of one or more skin constituents. Further, the hardware and/or software can comprise software for correcting and/or calibrating image non-linearities or distortions from the second optical path or discrepancies in a mechanical model used during image processing. Additionally, the computer hardware and/or software can be mechanically and electrically coupled to the camera of the device, including for processing image data and/or transmitting the image data for further processing, presentation, or display. In some embodiments, computer hardware and/or software includes a controller coupled to one or more components of the device, such as to the camera of the device. As described above, the camera can include an image recognition device or module that detects a component of skin (or a contrast agent associated with the skin component, as described further herein) and forms an image of the labeled or unlabeled component of the skin. Computer hardware and/or software of a device described herein can also include a processor configured to carry out one or more of the processes described above.

Moreover, computer hardware and/or software of a device described herein can be used to direct the device to begin laser or BBL treatment (e.g., ablation) at essentially "the same time" as the identification/localization of target constituents or components is ended. In other words, in some cases, imaging and treatment can occur sequentially, from a clinical perspective. For instance, in some cases, the laser or BBL treatment is begun 1 minute or less, 30 seconds or less, 20 seconds or less, 10 seconds or less, 5 seconds or less, 1 second or less, 0.5 seconds or less, or 0.1 seconds or less after the identification/imaging is ended. It is also possible, in some cases, for the laser or BBL treatment (e.g., laser ablation) to be carried out simultaneously or nearly simultaneously with the imaging/identification of target constituents, or partially temporally overlapping the imaging/identification. Thus, in some embodiments, a device described herein enables rapid diagnosis (or imaging) and treatment of a condition, such as a skin condition, in a sequential or non-sequential manner.

Devices described herein can also comprise one or more additional components other than those described above. For instance, in some cases, a device described herein further comprises one or more lenses, mirrors, and/or actuators. Any such lenses, mirrors, and/or actuators not inconsistent with the objectives of the present disclosure may be used. For example, in some embodiments, a device comprises one or more lenses, mirrors, and/or actuators for directing the light received from the optical aperture to the camera and/or for directing the laser or BBL beam to one or more desired locations on a surface of skin of a patient. Many suitable lenses, mirrors, actuators, or other hardware or software will be readily apparent to those of ordinary skill in the art.

It is further to be understood that a device described herein can have any combination of properties or features described hereinabove not inconsistent with the objectives of the present disclosure. Additionally, as stated above, it should be further noted that devices described herein can also be used to provide laser or BBL source light to surfaces or constituents or components of surfaces, or regions below surfaces, that may not be surfaces of skin of a human patient. For example, in some cases, a surface may be a surface of a non-biological material, such as a metal surface or a polymeric surface.

Moreover, it is to be understood that systems comprising the foregoing devices are contemplated herein. Such systems can further comprise one or more components in addition to a device described herein. For instance, a system can also include a power source, an image display device such as a screen or monitor, electrical cables and/or connectors, and/or one or more ergonomic structures for facilitating use of the device by a treatment provider such as a physician.

II. Methods of Treating Skin or a Component of Skin

In another aspect, methods of treating skin or a component, constituent, or structure of skin are described herein. It is to be understood that such methods, in some cases, can be carried out using devices described hereinabove in Section I. In some embodiments, for example, a method of treating skin or a component of skin comprises removing, ablating, vaporizing, destroying, or otherwise treating the skin or component of skin within a target area of a device described hereinabove in Section I, including by directing a laser or BBL beam onto the skin or component of skin from the device. Moreover, as described further herein, a method described herein can comprise labeling, imaging, detecting, and/or mapping the skin or component of skin prior to (or substantially simultaneously with) directing a laser or BBL beam onto the skin or component of skin for treatment purposes. Alternatively, in other instances, the structure of skin is not labeled but is instead imaged or detected in its "native" or natural state, without first labeling the structure. It may be especially desirable to omit a labeling step when the relevant structure of skin is visually discernible, including in a facile manner, without the use of a labeling agent. Additionally, as described further hereinbelow, a method described herein can be partially or fully automated if desired, including for implementation by a computer.

Turning now more particularly to specific steps of methods described herein, methods described herein comprise removing, ablating, vaporizing, destroying, or otherwise treating skin or a component, constituent, or structure of skin. Any component, constituent, or structure of skin not inconsistent with the objectives of the present disclosure may be treated by a method described herein. For example, in some cases, the structure of skin is a pore, gland, hair follicle, acne, skin lesion (which may be benign, premalignant, or malignant), blood vessel, or vascular lesion. Further, in some instances, the gland is an eccrine sweat gland, apocrine gland, or sebaceous gland. Other glands may also be targeted.

Methods described herein, in some embodiments, also comprise labeling a component, constituent, or structure of skin. Such labeling can be carried out in any manner not inconsistent with the objectives of the present disclosure. For example, in some cases, labeling comprises applying a contrast agent or dye to the structure of skin, which may be a pore or skin lesion. Labeling may also be carried out by marking with a pen or marker. Any contrast agent, dye, marker, or pen not inconsistent with the objectives of the present disclosure may be used. For instance, in some embodiments, the contrast agent is charged or ionic. A contrast agent can also be an organic contrast agent or dye. One non-limiting example of a contrast agent that can be used in a method described herein includes methylene blue. Other contrast agents may also be used. In addition, in some cases, applying a contrast agent to the structure of skin comprises applying a composition (such as a solution, cream, or paste) containing the contrast agent to the surface of the skin. Moreover, in some embodiments, a contrast agent is applied to the structure of the skin electrophoretically or using iontophoresis. For instance, in some cases, the contrast agent is delivered through the local application of an electrical current to the skin. The use of an electrical current or voltage may be especially preferred for labeling pores with a contrast agent such as methylene blue. Specific components, constituents, or structures of skin may be labeled in other manners as well, as understood by one of ordinary skill in the art.

Methods described herein also comprise directing or applying electromagnetic radiation to skin or a specific component, constituent, or structure of skin. Electromagnetic radiation can be applied to skin or a component, constituent, or structure of skin in any manner not inconsistent with the objectives of the present disclosure. For example, in some cases, the electromagnetic radiation is a laser or BBL beam produced by a device described in Section I hereinabove. Any such laser or BBL beam not inconsistent with the objectives of the present disclosure may be used. For example, in some cases, the electromagnetic radiation is applied by a laser or BBL source coupled to a camera and a controller.

More generally, various steps of a method described herein, in addition to the step of applying a laser or BBL beam to skin, or to a component or constituent of skin, can be carried out using a computer. Thus, in some embodiments, computer-implemented methods are described herein. In some cases, such a method is for identifying and determining characteristics of skin constituents so as to guide the appropriate delivery of therapeutic laser or BBL energy. In some instances, such a method comprises capturing one or more images with at least one camera (such as a digital camera described hereinabove). The camera can have a fixed or unvarying focal length. Additionally, if a plurality of cameras is used, each camera can have a fixed focal length, though the fixed focal lengths of the plurality of cameras can vary from one another. A method described herein can further comprise compensating for one or more optical distortions of the optical path of the camera that may be present. In some cases, the method also comprises cropping one or more of the one or more images, as needed or desired, and retaining only the portion of any cropped images that is relevant to therapy performed by the method. In some embodiments, the method further comprises identifying therapeutically pertinent skin constituents. Such constituents, in some instances, are identified by their spatial location, size, color, estimated depth beneath the surface of the skin, and/or estimated angle of shaft, in the event there is a shaft. A method described herein can further comprise mapping skin constituents and/or skin constituent characteristics (e.g., location) to a mechanical model of a positioning system of the laser or BBL source, such that the position of the laser or BBL source (and/or a laser or BBL beam provided by the laser or BBL source) is known relative to the position of the relevant skin constituents. Such a method can further comprise transmitting the skin constituent characteristics (e.g., location) to a controller of the laser or BBL source so that a laser or BBL beam can be directed to one or more skin constituents as desired by a user. It is to be understood that one or more of the foregoing steps of a computer-implemented method can be carried out using hardware and/or software described herein.

In addition, a method described herein can include placing one or more portions of a device described herein in direct contact with skin or a surface of skin to be imaged and/or treated. For example, in some instances, the bottom surface of an applicator described herein is placed in direct contact with the skin or surface of skin. In other cases, the aperture of the device is placed in directed contact with the skin or surface of skin.

As described above, methods described herein can be used to treat a variety of skin components, constituents, or structures, including to ameliorate a variety of skin conditions or other conditions in a human patient in need thereof. It is to be understood that the skin treated by a method described herein can be located on any region of the body of the patient not inconsistent with the objectives of the present disclosure. For example, in some cases, the treatment area of the skin is within the axillae, sole or palm. The foregoing regions of the body may be particularly suitable for the treatment of hyperhidrosis. Thus, in some embodiments, a method of treating hyperhidrosis is described herein.

Some embodiments described herein are further illustrated in the following non-limiting examples.

Example 1

Devices for Laser Treatment of Skin

Exemplary devices for laser treatment of skin according to some embodiments described herein are further described with reference to the drawings.

FIGS. 1, 2A, and 2B illustrate various aspects of a device for the laser treatment of skin. Referring to FIG. 1, a device, generally designated 100, for the image-guided laser treatment of different skin conditions is shown. Treatment of skin conditions can include, but is not limited to, sweat gland treatment and/or removal, hair treatment and/or removal, acne treatment and/or ablation, pigmented lesion treatment, vascular lesion treatment, skin cancer treatment and/or ablation, blood vessel treatment and/or removal, capillary treatment and/or removal, etc. Notably, device 100 is configured to laser treat precisely targeted areas of a patient's skin, where the precisely targeted areas are determined and/or identified via an image analysis system including a camera operating in the visible or infrared portions of the electromagnetic spectrum.

As FIG. 1 illustrates, device 100 includes an interior compartment 102 having a proximal end 102A (e.g., proximal to a user), a distal end 102B, and an optical aperture 104 disposed at and/or proximate to the distal end 102B. Device 100 is a handheld device configured to be grasped by a user (e.g., doctor, nurse, surgeon, medical practitioner, medical professional, etc.) during a laser therapy procedure to treat one or more lesions and/or constituents disposed on a patient's skin S. For example and during use, optical aperture 104 can be aimed by the user and face a surface of the patient's skin S to be treated.

A laser 106 can also be provided, disposed, and/or otherwise housed within a portion of interior compartment 102, for example, between the distal and proximal ends 102A, 102B. However, it is to be understood that laser 106 can be located inside or outside the interior compartment 102, or can be part of a system comprising the device 100, rather than being located within device 100 itself. In the event the laser 106 is located outside of the interior compartment 102 or the device 100, laser 106 is optically coupled to the device 100 and/or interior compartment 102. The skin S facing device 100 may include, without limitation, skin of the axillae, sole or palm. Such skin S may include one or more constituents (e.g., a hair, a pore, sweat gland, pigmented skin cell, blood vessel, vascular lesion, skin cancer, etc.) to be treated, removed, and/or ablated.

Laser 106 produces, or is positioned and/or configured to produce, a laser beam 106A of a first average wavelength. The first average wavelength is from about 100-12,000 nm or 600-12,000 nm, or any subrange therebetween (e.g., 600-800 nm, 1100-1400 nm, 1300-1500 nm, 1400-1600 nm, 2000-3000 nm, 2750-2950 nm, 9,000-11,000 nm, etc.), for example, depending upon whether the laser beam is ablative or non-ablative.

In certain embodiments, laser 106 produces a laser beam having a first average wavelength about 532 nm, about 694 nm, about 755 nm, about 1064 nm, about 1470 nm, about 1320 nm, about 1440 nm, about 1450 nm, about 1550 nm, about 2790 nm, about 2940 nm, or about 10,600 nm. Laser 106 can comprise an Erbium-based laser (e.g., an Er:YAG laser), a carbon dioxide ($CO_2$) laser, a Thulium (Tm) laser, a Neodymium-based laser (e.g., a Nd: YAG laser), or a combination thereof. As persons having skill in the art will appreciate, laser 106 can comprise any type of laser that is suitable for the non-invasive, ablative or non-ablative therapeutic treatment skin S consistent with the objectives of the instant disclosure, including but not limited to selective photothermolysis procedures.

As FIG. 1 further illustrates, laser beam 106A has a first optical path (i.e., shown in the uniform dashed line), which extends through and/or along a length of interior compartment 102. The first optical path extends between the respective proximal and distal ends 102A, 102B, and exits interior compartment 102 through optical aperture 104 towards skin S. Laser beam 106A can treat the patient's skin S via contacting and/or penetrating one or more layers thereof.

Device 100 can further comprise a camera 108. Camera 108 can be positioned or configured to receive light 108A of a second average wavelength from the optical aperture 104. In some embodiments, a light source LS can emit light towards the surface of the subject's skin S, and the light can be reflected off the skin back up through aperture 104 and received at camera 108. For example and in some embodiments, light 108A from the skin S is reflected through the aperture 104 and routed to the camera 108 via one or more optical elements (e.g., mirrors, lenses, dichroic filters, plates, etc.). The light 108A traverses a second optical path (i.e., shown in the dashed line consisting of short dashes) within interior compartment 102 between skin S and camera 108. Light 108A can have a second average wavelength of light that is, for example and without limitation, in the visible or infrared portions of the electromagnetic spectrum. For example, the second average wavelength of light can be from about 390 nm to 700 nm, or a subrange thereof (e.g., 450-520 nm, 520-620 nm, 600-700 nm, etc.) or from about 700 nm to 1 mm, or a subrange thereof (e.g., 700 nm-1050 nm, 1000 nm-2000 nm, 10000-50000 nm, etc.).

One or more optical elements are disposed and/or housed within interior compartment 102. For example, at least a first optical element 110 is disposed in interior compartment 102 between respective distal and proximal ends 102A, 102B. In certain embodiments, first optical element 110 comprises a selectively reflective plate that is placed, positioned, or disposed in the first and second optical paths. First optical element 110 is selectively reflective, meaning it can reflect some light (i.e., some wavelengths in the electromagnetic spectrum) and transmit other light (i.e., some other wavelengths in the electromagnetic spectrum).

For example and in some embodiments, at least about 70% of the total intensity of the laser beam 106A incident on the selectively reflective optical element 110 is transmitted. That is, first optical element 110 is at least 70% transparent to the first average wavelength of light associated with the laser beam 106A. Further, the selectively reflective optical element 110 reflects light 108A to the camera 108, and at least 1% of the total intensity of incident light 108A received from the optical aperture 104 is reflected and aimed towards camera 108. That is, first optical element 110 is at least 1% reflective of the second average wavelength of light 108A. Thus, first optical element 110 is selectively reflective, meaning it is reflective of the second average wavelength of light 108A, while simultaneously transmissive to the first average wavelength of light emitted associated with laser beam 106A.

In certain embodiments, first optical element 110 comprises a semi-reflective or dichroic plate disposed in the device 100 that advantageously combines laser delivery with imaging, as the plate is partially or fully transparent to the laser light (i.e., 106A) and partially or fully reflective of the imaging wavelength (i.e., light 108A). Laser beam 106A can pass through first optical element 110 and be delivered to a target area on the skin S, while the image reflected from the skin S as it passes through aperture 104 is reflected from first optical element 110 towards and/or to camera 108.

Device 100 can further comprise one or more additional optical elements disposed in interior compartment 102, including but not limited to one or more lenses, mirrors, and/or actuators for directing the light received from optical aperture 104 to camera 108 and/or for directing laser beam 106A to one or more desired locations on a patient's skin S. For example, at least a second optical element 112 can be disposed proximate distal end 102B of device 100 and opposite from the first optical element 110. Second optical element 112 can comprise a reflective plate or mirror that is fully or substantially fully reflective of light 108A and laser beam 106A. For example, second optical element 112 can reflect laser beam 106A towards skin S and reflect light 108A towards camera 108.

Still referring to FIG. 1 and in some embodiments, device 100 further comprises an applicator 114 attached to the distal end 102A of interior compartment 102. Applicator 114 may attach to and/or extend from a portion of aperture 104 and/or optionally be at least partially received therein. Applicator 114 is configured to couple, connect, or attach device 100 to a surface of the patient's skin S to facilitate treatment of a certain area of the patient's skin. Applicator 114 can connect to device 100 via a connecting portion or member 115. Connecting member 115 can comprise a leg disposed on one side of applicator 114, or a circular, cylindrical, and/or conical member that surrounds portions of the optical actuator 104 to aim and/or contain laser beam 106A.

In some embodiments, applicator 114 can comprise or be formed of metal, plastic, or combinations thereof and conform to portions of the patient's skin S during use. For example, applicator 114 can define an imaging area A on the skin S as a bottom surface 116 of applicator contacts the skin S. The bottom surface 116 of applicator 114 can comprise a window (FIGS. 2A, 2B) by which an affected portion P of skin is viewed and/or imaged. An image I of the affected portion P of the patient's skin is transmitted to camera 108 and displayed on a display 118. Notably, device 100 combines imaging and laser techniques for therapeutically treating specific constituents on a patient's skin via an easily manipulated hand held device. Device 100 includes and/or is connected to a computing platform CP comprising computer hardware and/or executing computing software for identifying a spatial location of one or more constituents in affected portion P of skin S proximate the distal end of the device.

FIGS. 2A and 2B are respective plan and sectional views of device applicator 114. FIG. 2A is a plan view of bottom surface 116 of applicator 114. Bottom surface 116 is configured to be positioned adjacent and/or in contact with a patient's skin (i.e., S, FIG. 1), and over, on, and/or around an affected area or portion (i.e., P, FIG. 1) thereof, which contains one or more constituents to be imaged and targeted for laser application. Applicator 114 connects to device 100 via connecting member 115.

Referring collectively FIGS. 2A and 2B, bottom surface 116 comprises a window 120 that is substantially transparent to both the laser beam (i.e., 106A, FIG. 1) and light (i.e., 108A, FIG. 1) received by the camera. An affected area or portion (e.g., P, FIG. 1) of the patient's skin can be aligned and disposed in window 120 during treatment, so that the affected area can be imaged and displayed on a screen for facilitating precisely targeted laser therapy applied to specific constituents (e.g., hair follicles, pores, pigmented skin cells, abnormal skin cells, sweat glands, etc.) of the affected area. Bottom surface 116 can be substantially flat and/or planar, but also configured to conform to a surface of the patient's skin during use.

In some embodiments, an adhesive is applied to bottom surface 116 of device 100 for temporarily and/or reversibly adhering the bottom surface 116 of applicator 114 to the patient's skin during treatment. This can minimize movement of the device, skin, and/or otherwise stabilize applicator 114 during treatment. An exemplary adhesive comprises cyanoacrylate.

In further embodiments, applicator 114 comprises a non-permeable chamber 122 that, upon application of a vacuum, causes portions 124 of bottom surface 116 to form one or more hermetic seals with the surface of the skin. That is, when a vacuum is applied, portions 124 of bottom surface 116 can hermetically seal to or against the skin's surface for improved targeting and stabilization during a laser therapy procedure. Chamber 122 can be in fluid communication with a vacuum pump (not shown) via a fitting 126 for establishing a vacuum within the interior of non-permeable chamber 122.

As applicator 114 is brought into contact with the skin, the device is aligned so that target skin constituents (i.e., in portion P, FIG. 1) are visible through applicator window 120 and displayed on a screen for application of targeted laser therapy. Then, in certain embodiments, a vacuum pump connected to chamber 122 fitting 126 is activated for sealing applicator 114 to the patient's skin. The vacuum level in chamber 122 can provide firm attachment of the applicator to the skin, and at the same time be comfortable enough for the patient. In some embodiments, a vacuum of about 10-40% or 10-20% of the atmospheric pressure is applied to chamber 120, where desired.

Example 2

Systems for Laser or BBL Treating Skin

FIG. 3 is a block diagram of an exemplary system, generally designated 300, for laser or BBL treating skin. System 300 can comprise an image-guided laser or BBL treatment device 302 and a controller 304. It is understood that controller 304 is a special purpose computer configured to improve the technological field of imaging and light therapy treatments. Such improvements are manifested in terms of improved targeting and light treatment of individual skin constituents (e.g., individual skin cells, cancer cells, pigmented cells, individual pigmented lesions, individual pores, individual sweat glands, etc.). As FIG. 3 illustrates, device 302 and controller 304 can be separate (e.g., physically separate, non-integrated, discrete) entities or components. However, a system comprised of a device 302 that is integrated with a controller 304 is also contemplated.

Device 302 can comprise an imaging system (IS) 306 and a treatment system (TS) 308. Notably, IS 306 and TS 308 can collectively improve the targeting and treatment of discrete (i.e., individualized) skin constituents (e.g., sweat glands, pores, pigmented lesions, etc.), without having a significant effect on the skin that surrounds the discrete skin constituents.

In some embodiments, IS 306 is a camera (e.g., a digital camera) for imaging the skin and TS 308 is a laser or BBL source (e.g., a $CO_2$ laser, Er:YAG laser, etc.) for treating the skin. Device 302 is moved or guided relative to the patient's skin according to instructions received from controller 304. As device 302 moves, controller 304 instructs TS 308 to generate a laser or BBL beam, that device 302 can direct, treat and apply to individual skin constituents (e.g., sweat glands, pores, pigmented lesions, etc.). The instructions received at device 302 from controller 304 are formulated from imaging data 310 that is collected and/or received via IS 306 and then communicated and processed at controller 304. IS 306 collects or captures imaging data 310 using a camera and then sends the imaging data 310 to controller 304. Device 302 and controller 304 can electrically communicate using either a wired or wireless connection. Imaging data 310 can include, for example and without limitation, digital data that is representative of the presence and/or spatial locations of labeled skin constituents relative to the areas or locations of non-labeled skin.

Controller 304 is configured to receive, as input, imaging data 310 and construct a digitized map of the labeled skin conditions. For example, controller 304 can comprise a processor 312 configured to execute a feature recognition module 316 stored in the memory 314 of controller 316. Feature recognition module 316 is configured to input imaging data 310 and construct a digitized map of the labeled skin constituents relative to the area of skin to be treated. The locations of the mapped constituents correspond to coordinates that identify points for laser or BBL ablation and/or laser or BBL treatment allowing for improved, targeted treatment of individually mapped skin constituents.

Controller 304 can output (e.g., via a wired or wireless connection) control signals or commands instructing device 302 to move to positions or locations relative to the patient's skin that are centered over one of the desired coordinates corresponding to a labeled skin constituent. Once device 302 is in a desired position, controller 304 can output control signals or commands instructing TS 308 to generate a laser or BBL beam to individually treat such constituents via ablative or non-ablative light therapy.

As FIG. 3 illustrates, the subject matter described herein can be implemented in software in combination with hardware and/or firmware. For example, the subject matter described herein can be implemented in software executed by a processor. As used herein, the terms "function" and "module" refer to hardware, firmware, or software in combination with hardware and/or firmware for implementing features described herein. In an exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A device for light treatment of skin, the device comprising:
   an interior compartment having a proximal end and a distal end;
   an optical aperture disposed at the distal end;
   a laser or Broad Band Light (BBL) source that produces a laser or BBL beam, the laser or BBL beam having a first optical path within the interior compartment between the proximal end and the distal end and exiting the interior compartment through the optical aperture;
   a camera that receives light from the optical aperture, the light having a second optical path within the interior compartment; and
   a selectively reflective optical element disposed in the first optical path and in the second optical path,
   wherein the selectively reflective optical element transmits at least 70% of the laser or BBL beam incident on the selectively reflective optical element, and
   wherein the selectively reflective optical element reflects to the camera at least 1% of incident light received from the optical aperture.

2. A method of treating a target area of skin, the method comprising:
   providing the device of claim 1;
   imaging a set of components of skin for the target area, the imaging comprising receiving a return signal via an optical aperture of the device; and
   directing a laser or Broad Band Light (BBL) beam onto the target area through the optical aperture based at least in part on the imaging.

3. The method of claim 2, further comprising labelling at least a portion of the set of components of skin.

4. The method of claim 2, wherein the imaging further comprises producing a query beam that exits the optical aperture of the device toward the target area.

5. The method of claim 2, further comprising placing the aperture of the device in direct contact with the target area.

6. The method of claim 2, further comprising coupling the device to the surface of skin of a patient via an applicator.

7. The method of claim 2, further comprising determining the position of the device relative to the target area.

8. The method of claim 2, wherein the imaging is carried out with an acoustic imaging system.

9. The method of claim 2, wherein the imaging is carried out with a camera.

10. The method of claim 2, further comprising identifying at least one of a class, size, shape, color, estimated depth, or shaft angle of a component of skin.

11. The method of claim 2, wherein the laser or BBL beam is ablative or non-ablative.

12. The method of claim 2, further comprising correcting and/or calibrating image non-linearity or distortions associated with the imaging.

* * * * *